United States Patent [19]

Gummesson et al.

[11] Patent Number: 4,762,618
[45] Date of Patent: Aug. 9, 1988

[54] APPARATUS AND METHOD FOR CONTROLLING FLUID FLOW IN DIALYSIS AND THE LIKE

[75] Inventors: Bengt-Ake G. Gummesson, Bara; Preben A. Petersen, Bjarred; Jan P. Sternby, Lund, all of Sweden

[73] Assignee: Gambro AB, Sweden

[21] Appl. No.: 868,803

[22] Filed: May 29, 1986

[30] Foreign Application Priority Data

Jun. 4, 1985 [SE] Sweden .................. 85.02757

[51] Int. Cl.$^4$ .................................. B01D 13/00
[52] U.S. Cl. .................. 210/637; 210/646; 210/741; 210/110; 210/134; 210/137; 210/321.65
[58] Field of Search ........... 210/637, 646, 741, 927, 210/90, 110, 134, 137, 321.2, 321.3

[56] References Cited

U.S. PATENT DOCUMENTS

| | | | |
|---|---|---|---|
| 4,021,341 | 5/1977 | Cosentino et al. | 210/929 X |
| 4,113,614 | 9/1978 | Rollo et al. | 210/90 X |
| 4,122,010 | 10/1978 | Riede et al. | 210/90 |
| 4,158,034 | 6/1979 | Riede et al. | 210/321.3 |
| 4,191,359 | 3/1980 | Andersson et al. | 269/237 X |
| 4,191,646 | 3/1980 | Larsson et al. | 210/103 |
| 4,194,974 | 3/1980 | Jonsson | 210/90 |
| 4,267,041 | 5/1981 | Schael | 210/929 X |
| 4,293,409 | 10/1981 | Riede et al. | 210/96.2 |
| 4,370,983 | 2/1983 | Lichtenstein | 210/321.2 X |
| 4,536,201 | 8/1985 | Brorsson et al. | 210/257.2 |
| 4,585,552 | 4/1986 | Summesson et al. | 210/87 |

FOREIGN PATENT DOCUMENTS

| | | |
|---|---|---|
| 22922 | 1/1981 | European Pat. Off. |
| 106940 | 5/1984 | European Pat. Off. |
| 2003274 | 3/1979 | United Kingdom |

*Primary Examiner*—Frank Sever
*Attorney, Agent, or Firm*—Lerner, David, Littenberg, Krumholz & Mentlik

[57] ABSTRACT

Apparatus and methods are disclosed for controlling the flow of a fluid past a membrane in a dialyzer. The apparatus disclosed includes a fluid conduit for conducting the fluid both towards and away from the dialyzer, a flow constrictor for creating a pressure drop in the fluid conduit either upstream or downstream of the dialyzer, a pump for pumping the fluid through that conduit, and a pressure detector for measuring a pressure corresponding to that pressure drop so as to control the flow therein. The method disclosed includes flowing the fluid through an upstream fluid conduit to the dialyzer and through a downstream fluid conduit away from the dialyzer, producing a relatively constant flow in both the upstream and downstream fluid conduits, creating a pressure drop in one of the fluid conduits, pumping the fluid through that conduit, and measuring the pressure corresponding to that pressure drop so that the flow of the fluid in that conduit can be controlled thereby.

28 Claims, 1 Drawing Sheet

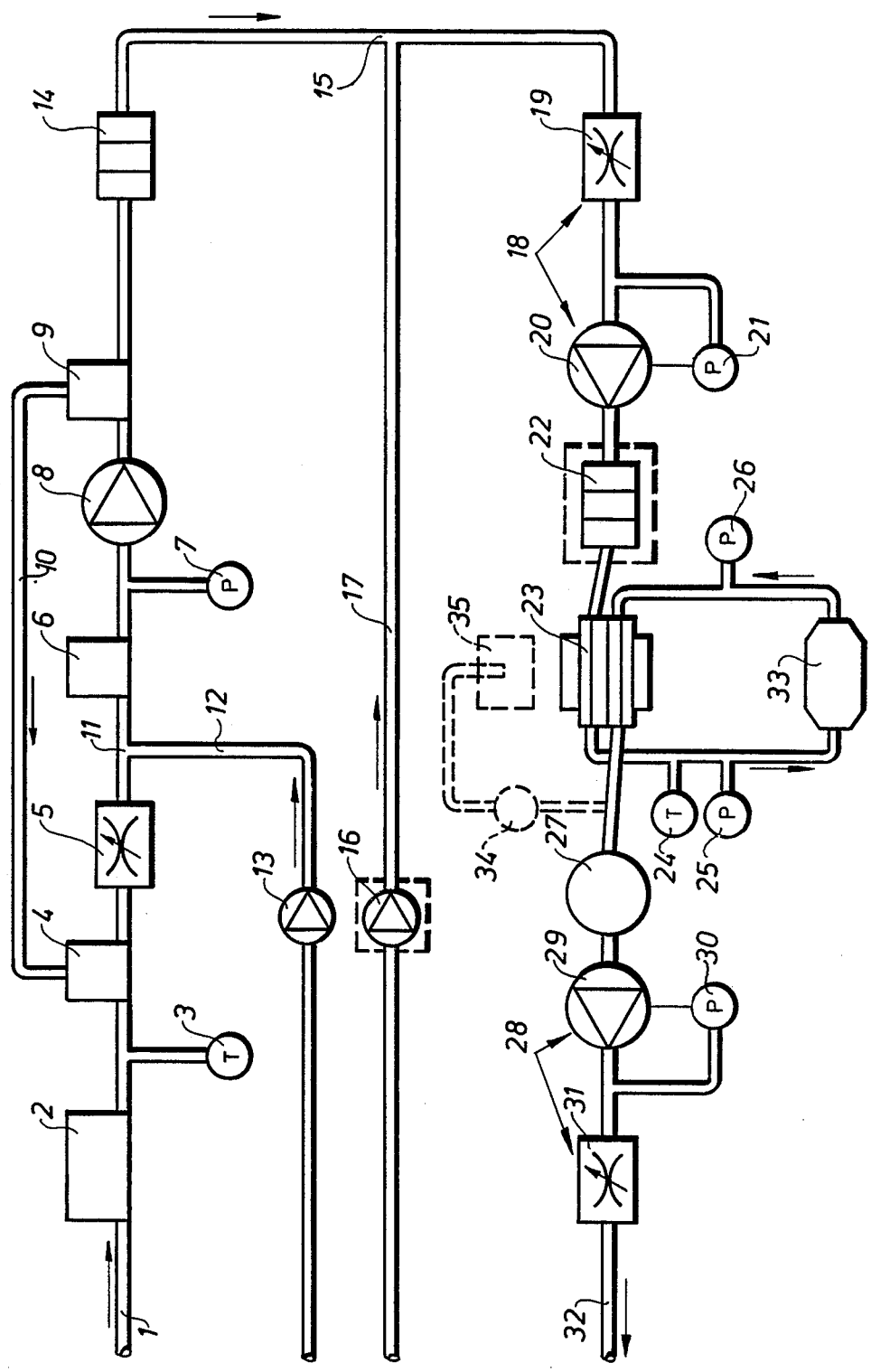

APPARATUS AND METHOD FOR CONTROLLING FLUID FLOW IN DIALYSIS AND THE LIKE

FIELD OF THE INVENTION

The present invention relates to apparatus and methods for controlling fluid flow in dialysis and the like, and especially the ultrafiltration conducted in such devices. More particularly, the present apparatus relates to means for operation of a dialyzer and the like, and means for monitoring and controlling respective fluid flows on both sides of a membrane included in such a dialyzer. The present invention also relates to methods for controlling the flow of fluid in dialyzers and the like.

Still more particularly, the present invention relates to apparatus and methods for controlling hemodialysis, more particularly for purifying the blood of a patient with diminished or nil renal function. More particularly, the present invention is directed to apparatus and methods for controlling dialysis in general.

BACKGROUND OF THE INVENTION

This invention particularly relates to an improvement in the system currently being marketed by the Gambro Group, to which the assignee of the present application belongs, under the description "Gambro AK-10".

Various details of this system form the subject, for example, of U.S. Pat. Nos. 4,122,010, 4,158,034, 4,293,409, 4,194,974, and 4,191,359, and the descriptions of this system referred to therein are incorporated herein by reference thereto, and further improvements thereon are disclosed in U.S. Pat. No. 4,536,201, British Pat. No. 2,003,274 and the European patent application published under No. EP 0 106 940. Reference is also made to EP 0 022 922 which describes in more detail the preparation of dialysis fluid from two concentrates, a preparation which is only touched upon in the following description of the present invention.

SUMMARY OF THE INVENTION

In accordance with the present invention, applicants have discovered an apparatus and method for controlling the flow of a fluid past a membrane in a dialyzer. In accordance with the apparatus of the present invention, there is provided fluid conduit means for conducting a flow of fluid towards and away from the dialyzer, first constant flow means for producing a first relatively constant flow in the fluid conduit means upstream of the dialyzer, and second constant flow means for producing a second relatively constant flow in the fluid conduit means downstream of the dialyzer, at least one of the first and second constant flow means comprising constriction means for creating a pressure drop in the flow of the fluid in the fluid conduit means, pump means for pumping the fluid through the fluid conduit means, and pressure measuring means for measuring a pressure corresponding to the pressure drop created by the constriction means whereby at least one of the first and second constant flow means can be controlled thereby.

In accordance with a preferred embodiment of the apparatus of the present invention, ultrafiltration is carried out across the membrane in the dialyzer whereby control of one of the constant flow means controls the rate of ultrafiltration in the dialyzer.

In accordance with another embodiment of the apparatus of the present invention, the pressure measuring means measures the pressure in the fluid conduit means at a point between the pump means and the constriction means. Preferably, the pressure in the fluid on the side of the constriction means opposite that of the pressure measuring means is maintained substantially constant, and most preferably at atmospheric pressure.

In accordance with another embodiment of the apparatus of the present invention, the apparatus includes pump control means responsive to the pressure measuring means so that the capacity of the pump means can be controlled in response to the pressure measured by the pressure measuring means.

In accordance with a preferred embodiment of the apparatus of the present invention, second constant flow means are provided, again including a second constriction means, pump means, and pressure measuring means so that both the first and second constant flow means can be controlled thereby.

In accordance with the method of the present invention, there is provided the steps of flowing a fluid through an upstream fluid flow portion to a dialyzer and from the dialyzer through a downstream fluid flow portion, producing a first relatively constant flow in the upstream fluid flow portion, producing a second relatively constant flow in the downstream fluid flow portion, creating a pressure drop in at least one of the upstream and downstream fluid flow portions, pumping the fluid through that fluid flow portion, and measuring a pressure corresponding to the pressure drop in that fluid flow portion whereby the flow of the fluid in that fluid flow portion can be controlled thereby.

In accordance with another embodiment of the method of the present invention, the method includes conducting ultrafiltration across the membrane in the dialyzer so that control of one of the fluid flow portions can also control the rate of ultrafiltration in the dialyzer.

In accordance with another embodiment of the method of the present invention, the method includes controlling the pumping of the fluid through at least one of the upstream and downstream fluid flow portions in response to measuring of the pressure corresponding to the pressure drop created therein.

In accordance with another embodiment of the method of the present invention, the method includes creating pressure drops in both the upstream and downstream portions, pumping the fluid through both the upstream and downstream portions, and measuring a pressure corresponding to both such pressure drops so that the flow of the fluid in both the upstream and downstream fluid flow portions can be controlled thereby.

In accordance with the method of the present invention, the method includes flowing a fluid through an upstream fluid flow portion to the dialyzer and from the dialyzer through a downstream fluid flow portion, producing a first relatively constant flow in the upstream fluid flow portion, producing a second relatively constant flow in the downstream portion, creating a pressure drop in at least one of the upstream and downstream fluid flow portions, pumping the fluid through that fluid flow portion, and measuring a pressure corresponding to that pressure drop, whereby the flow of the fluid in the upstream or downstream fluid flow portion can be controlled thereby. In accordance with one embodiment of the method of the present invention, the method includes conducting ultrafiltration across the membrane in the dialyzer whereby control of the upstream and/or downstream fluid flow portions also controls the rate of ultrafiltration in the dialyzer.

In accordance with another embodiment of the method of the present invention, the method includes controlling the pumping of the fluid through the upstream and/or downstream fluid flow portions in response to measuring of the pressure corresponding to the pressure drop therein.

In accordance with another embodiment of the method of the present invention, the method includes creating a pressure drop in both the upstream and downstream fluid flow portions, pumping the fluid through both of those fluid flow portions, and measuring a pressure corresponding to those pressure drops, whereby the flow of fluid in both the upstream and downstream fluid flow portions can be controlled thereby.

The present invention thus relates to a system which is characterized by two constant flow arrangements for the control of one or both of the fluid flows located before and after the dialyzer. In accordance with this invention, a very rapid control is made possible which can be carried out independently of the transmembrane pressure (TMP) across the membrane in the dialyzer. The TMP is, in other cases, frequently used for control of the ultrafiltration, but this normally provides a rather slow control factor in view of, among other things, the resilience of the membrane in the dialyzer.

At least one of the two constant flow arrangements should be controllable in accordance with this invention so as to control the ultrafiltration taking place in the dialyzer. As will be evident from the following description, however, there is another possible alternative.

In accordance with the present invention, the controllable constant flow arrangement preferably comprises a pump and a constriction coupled in series, and means for measuring a pressure which is a function of the pressure drop over the constriction, and which is thus also a function of the flow therethrough. The pressure which is thus measured consists of that in the fluid flow between the pump and the constriction, while the pressure on the other side of the constriction is preferably held constant, e.g. at atmospheric pressure. In such a design the pressure thus measured may then be used to control the capacity of the pump, and this can be done in a fraction of a second. If control is to be achieved by altering the voltage of the motor, the time between such alteration of the voltage and concomitant alteration of the fluid flow may be in the order of magnitude of about 0.1 sec. As a result, the system can also cope with pressure surges, which in many known systems has given rise to uncontrollable ultrafiltration.

The two constant flow arrangements of the present invention are preferably of an essentially identical design and capacity, but they are individually controllable independently of each other. This simplifies the overall design, while at the same time providing freedom to operate at both varying total flow and varying pressure. The overall control is also made simpler if identical constant flow arrangements are used.

In accordance with another aspect of the present invention, and for reasons of safety, means for measuring the pressure in the dialysis fluid flow are also provided, at least on one side of the dialyzer (i.e.—between the dialyzer and the respective constant flow arrangement) for checking and/or controlling the transmembrane pressure (TMP). At the same time, the blood pressure on the other side of the membrane can also be measured.

In accordance with another embodiment of the present invention, the system also comprises means for measurement of the dialysis fluid flow both before and after the dialyzer. This means may, for example, comprise a differential measuring arrangement for directly measuring the difference in the fluid flow before (upstream) and after (downstream) the dialyzer. This difference can preferably be adapted to be integrated, and thus used to control one or both of the constant flow arrangements. The measuring system itself is described in greater detail in British Pat. No. 2,003,274 and in U.S. Pat. No. 4,585,552.

In accordance with a preferred embodiment of this aspect of the present invention, the differential measuring arrangements can be used to counteract slow alterations in the ultrafiltration which are caused, for example, by membrane offset, while one or both of the constant flow arrangements can be used to counteract rapid alterations in the ultrafiltration which are caused, for example, by accidental pressure surges. As a result, a very reliable control of the ultrafiltration is obtained, which is also substantially independent of any accidental pressure surges therein.

Similar such advantages may be obtained by instead making use of the measured TMP in order to counteract slow alterations in the ultrafiltration, such as those caused by drift of the measuring instrument being used, while one or both of the constant flow arrangements is used to counteract rapid alterations in the ultrafiltration which are caused, for example, by accidental pressure surges.

In an alternative embodiment, the two constant flow arrangements are adapted to maintain the same constant flow, and at the same time the ultrafiltration is adapted to be controlled through withdrawal of ultrafiltrate between the two constant flow arrangements by means of a controllable ultrafiltrate pump.

BRIEF DESCRIPTION OF THE DRAWINGS

The present invention is described in more detail in the following Detailed Description which refers to the drawing, which shows an example of the most important components of a system in accordance with the present invention.

DETAILED DESCRIPTION

Referring to the drawing, in the example of the invention shown therein water is fed through inlet 1 to a heating device 2, where it is heated. The temperature of the fluid is then measured in a temperature measuring device 3 before the water-containing fluid is conducted through a return vessel 4 to a constriction 5, and then through a bubble expansion tank 6, a pressure gauge 7, and a pump 8, to a vent tank 9. From vent tank 9 a return duct 10 leads back to return vessel 4 in order to accomplish the recycle of any air or other gases which are separated. Such recycling could also possibly be made instead to the heating vessel 2, but doing so would then require that the return duct 10 be made from a more resistant material, since dialysis concentrate is being supplied to point 11 through duct 12, with the help of pump 13. This portion of this system substantially corresponds to the system described, for example, in U.S. Pat. Nos. 4,158,034 and 4,293,409. Also, the function of expansion vessel 6 is described in detail in U.S. Pat. No. 4,536,201. From vent tank 9 the fluid is then passed through conductivity measuring cell 14 to another mixing point 15, where further concentrate is supplied, in this case possibly with the assistance of a pump 16 and a duct 17. This is done where it is intended to work with a so-called two-component-based dialysis concentrate, e.g. of the type described in EP No. 0 022 922.

From mixing point 15 the dialysis fluid is then passed through a first constant flow arrangement 18, which consists of constriction 19, pump 20 and pressure gauge 21. Before (upstream of) the constriction device 19 the pressure is substantially at atmospheric pressure, as this duct is connected to the vent tank 9 without any major resistance. Should it be found in practice that there is a variation in pressure due to the pump 16, the conductivity meter 14 and the mixing point 15 can be moved to a position prior to (upstream of) the vent tank 9.

The pressure measured by pressure gauge 21 can then be used to control the pump 20, so that a desired constant flow can thus be obtained. Downstream of the pump 20 the fluid passes through a conductivity meter 22 and an ultrafiltration monitor 23, and then through a temperature measuring instrument 24 and a pressure gauge 25, to the dialyzer 33. From the dialyzer the fluid flow is then conducted through a pressure gauge 26, the ultrafiltration monitor 23, and a blood detector 27, to a further constant flow arrangement 28, in this case consisting of a pump 29, a pressure gauge 30 and a constriction device 31. Finally, the dialysate is passed to an outlet 32. It is preferred that the constant flow arrangement 28 be identical to the constant flow arrangement 18. In the constriction 31, however, the pressure drop which is obtained is from a pressure which is above atmospheric to the pressure prevailing at the outlet, which should be kept constant and, for example, may be equal to atmospheric pressure.

The design and the function of the ultrafiltration monitor 23 are described in greater detail in the above-mentioned publication, namely British Pat. No. 2,033,274 and U.S. Pat. No. 4,585,552.

Reference numeral 33 designates the dialyzer, which can be connected to the system in accordance with the invention. The patient is thus connected to the blood side of the dialyzer 33. This latter connection, however, is not shown in the drawing. Finally, the broken lines in the drawing illustrate how ultrafiltrate can be withdrawn between the two constant flow arrangements 18 and 28 with the assistance of a pump 34, and possibly be collected in receiver vessel 35. In this manner the ultrafiltration rate can be appropriately controlled in that the two constant flow arrangements 18 and 28 are adapted to produce identical flows, so that the ultrafiltration can be wholly controlled by means of pump 34.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. Apparatus for controlling the flow of a fluid past one side of a membrane in a dialyzer comprising means for providing very rapid control independent of transmembrane pressure (TMP), including, fluid conduit means for conducting said flow of said fluid towards and away from said dialyzer, first constant flow means for producing a first constant flow in said fluid conduit means upstream of said dialyzer, and second constant flow means for producing a second constant flow in said fluid conduit means downstream of said dialyzer, said first constant flow means comprising first constriction means for creating a pressure drop in the flow of said fluid in said fluid conduit means from a first predetermined substantially constant pressure to a second lower pressure, pump means downstream of said first constriction means for pumping said fluid through said fluid conduit means, and pressure measuring means for measuring said second lower pressure, said second constant flow means comprising second constriction means for creating a pressure drop in the flow of said fluid in said fluid conduit means from a third pressure to a fourth predetermined substantially constant lower pressure, pump means upstream of said second constriction means for pumping said fluid through said fluid conduit means, and pressure measuring means for measuring said third pressure whereby said first and second constant flow means can be controlled thereby, based upon said measured second pressure and said measured third pressure, respectively.

2. The apparatus of claim 1 wherein said membrane in said dialyzer is an ultrafiltration membrane, said controlling of the flow of said fluid in said first and second constant flow means thereby controlling the rate of said ultrafiltration in said dialyzer.

3. The apparatus of claim 2 including fluid flow measuring means for measuring the flow of said fluid at first and second predetermined locations, said first predetermined location being upstream of said dialyzer and downstream of said first constant flow means, and said second predetermined location being downstream of said dialyzer and upstream of said second constant flow means.

4. The apparatus of claim 3 wherein said fluid flow measuring means comprises differential measuring means for directly measuring the difference in said fluid flow at said first and second predetermined locations, whereby said difference can be integraded and utilized to control said first and second constant flow means.

5. The apparatus of claim 4 including first ultrafiltration offset control means for controlling said first and second constant flow means in response to differences measured in said fluid flow reflecting changes in the rate of said ultrafiltration.

6. The apparatus of claim 1 wherein said pressure measuring means measures the pressure in said fluid conduit means at a point between said pump means and said constriction means.

7. The apparatus of claim 1 including vent means and outlet means, said first constriction means being connected to said vent means, and said second constriction means being connected to said outlet means, said vent means and said outlet means being maintained at a predetermined substantially constant pressure which comprises atmospheric pressure.

8. The apparatus of claim 1 including pump control means responsive to said pressure measuring means whereby the capacity of said pump means can be controlled in response to said pressure measured by said pressure measuring means.

9. The apparatus of claim 1 wherein said constriction means comprises first constriction means, said pump means comprises first pump means, and said pressure measuring means comprises first pressure measuring means, said first constant flow means thereby comprising said first constriction means, said first pump means, and said first pressure measuring means, and said second constant flow means comprising second constriction means for creating a pressure drop in the flow of said fluid in said fluid conduit means from a third pressure to a fourth predetermined substantially constant lower pressure, second pump means for pumping said fluid through said fluid conduit means, and second pressure measuring means for measuring said third pressure, whereby both said first and second constant flow means can be controlled thereby.

10. The apparatus of claim 9 wherein said membrane in said dialyzer is an ultrafiltration membrane, whereby said control of said first and second constant flows can control the rate of said ultrafiltration in said dialyzer, and including fluid withdrawal means for withdrawal of said fluid between said first and second constant flow means, said fluid withdrawal means comprising withdrawal fluid means and withdrawal pump fluid means for regulating the withdrawal of said fluid by said withdrawal fluid pump means, whereby said first and second constant flows can be maintained substantially constant and the rate of said ultrafiltration can be controlled by said fluid withdrawal means.

11. The apparatus of claim 1 including fluid flow pressure measuring means at a predetermined location between said first and second constant flow means and said dialyzer for measuring the pressure in said fluid conduit means at said predetermined location.

12. The apparatus of claim 11 including second ultrafiltration offset control means for controlling said first and second constant flow means in response to changes in said measured pressure in said fluid flow reflecting changes in the rate of said ultrafiltration.

13. A method for controlling the flow of a fluid past one side of a membrane in a dialzyer comprising providing very rapid control, independent of transmembrane pressure (TMP), by, flowing said fluid through an upstream fluid flow portion to said dialyzer and from said dialyzer through a downstream fluid flow portion, producing a first constant flow in said upstream fluid flow portion, producing a second constant flow in said downstream portion, creating a pressure drop at a first predetermined location in said upstream fluid flow portion from a first predetermined substantially constant pressure to a second lower pressure, pumping said upstream fluid flow portion from a position downstream of said first predetermined location, measuring said second lower pressure, creating a pressure drop at a second predetermined location in said downstream fluid flow portion from a third pressure in a fourth predetermined substantially constant lower pressure, pumping said downstream fluid flow portion from a position upstream of said second predetermined location, measuring said third pressure, and controlling the flow of said fluid in said upstream and downstream fluid flow portions, based upon said measured second pressure and said measured third pressure, respectively.

14. The method of claim 13 including conducting ultrafiltration across said membrane in said dialyzer, said controlling of said flow of said fluid in said upstream and downstream fluid flow portions thereby controls the rate of said ultrafiltration in said dialyzer.

15. Apparatus for controlling the flow of a fluid past one side of a membrane in a dialyzer comprising means for providing very rapid control independent of transmembrane pressure (TMP), including, fluid supply means for supplying a flow of a predetermined quantity of fluid, fluid conduit means for conducting said flow of said entire predetermined quantity of said fluid towards and away from said dialyzer, first constant flow means for producing a first constant flow in said fluid conduit means upstream of said dialyzer, and second constant flow means for producing a second constant flow in said fluid conduit means downstream of said dialyzer, said first constant flow means comprising first constriction means for creating a pressure drop in the flow of said entire predetermined quantity of said fluid in said fluid conduit means from a first predetermined substantially constant pressure to a second lower pressure, pump means downstream of said first constriction means for pumping said entire predetermined quantity of said fluid through said fluid conduit means, and pressure measuring means for measuring said second lower pressure, said second flow means comprising second constriction means for creating a pressure drop in the flow of said entire predetermined quantity of said fluid in said fluid conduit means from a third pressure to a fourth predetermined substantially constant lower pressure, pump means upstream of said second constriction means for pumping said entire predetermined quantity of said fluid through said fluid conduit means, and pressure measuring means for measuring said third pressure whereby said first and second constant flow means can be controlled thereby, based upon said measured second pressure and said measured third pressure, respectively.

16. The apparatus of claim 15 wherein said membrane in said dialyzer is an ultrafiltration membrane, said controlling of the flow of said fluid in said first and second constant flow means thereby controlling the rate of said ultrafiltration in said dialyzer.

17. The apparatus of claim 16 including fluid flow measuring means for measuring the flow of said fluid at first and second predetermined locations, said first predetermined location being upstream of said dialyzer and downstream of said first constant flow means, and said second predetermined location being downstream of said dialyzer and downstream of said second constant flow means.

18. The apparatus of claim 17 wherein said fluid flow measuring means comprises differential measuring means for directly measuring the difference in said fluid flow at said first and second predetermined locations, whereby said difference can be integrated and utilized to control said first and second constant flow means.

19. The apparatus of claim 18 including first ultrafiltration offset control means for controlling said first and second constant flow means in response to differences measured in said fluid flow reflecting changes in the rate of said ultrafiltration.

20. The apparatus of claim 15 wherein said pressure measuring means measures the pressure in said fluid conduit means at a point between said pump means and said constriction means.

21. The apparatus of claim 15 including vent means and outlet means, said first constriction means being connected to said vent means, and said second constriction means being connected to said outlet means, said vent means and said outlet means being maintained at a predetermined substantially constant pressure which comprises atmospheric pressure.

22. The apparatus of claim 15 including pump control means responsive to said pressure measuring means whereby the capacity of said pump means can be controlled in response to said pressured measure by said pressure measuring means.

23. The apparatus of claim 15 wherein said constriction means comprises first constriction means, said pump means comprises first pump means, and said pressure measuring means comprises first pressure measuring means, said first constant flow means thereby comprising said first constriction means, said first pump means, and said first pressure measuring means, and said constant flow means comprising second constriction means for creating a pressure drop in the flow of said fluid in said fluid conduit means from a third pressure to a fourth predetermined substantially constant lower pressure, second pump means for pumping said fluid through said fluid conduit means, and second pressure measuring means for measuring said third pressure whereby both first and second constant flow means can be controlled thereby.

24. The apparatus of claim 23 wherein said membrane in said dialyzer is an ultrafiltration membrane, whereby said control of said first and second constant flow means can control the rate of said ultrafiltration in said dialyzer and including fluid withdrawal means for withdrawal of said fluid between said first and second constant flow means, said fluid withdrawal means comprising withdrawal fluid pump means and withdrawal fluid pump control means for regulating the withdrawal of said fluid by said withdrawal fluid pump means, whereby said first and second constant flow means can be maintained substantially constant and the rate of said ultrafiltration can be controlled by said fluid withdrawal means.

25. The apparatus of claim 15 including fluid flow pressure measuring means at a predetermined location between said first and second constant flow means and said dialyzer for measuring the pressure in said fluid conduit means at said predetermined location.

26. The apparatus of claim 25 including second ultrafiltration offset control means for controlling said first and second constant flow means in response to changes in said measured pressure in said fluid flow reflecting changes in the rate of said ultrafiltration.

27. A method for controlling the flow of a fluid past one side of a membrane in a dialyzer comprising providing very rapid control, independent of transmembrane pressure (TMP), by, providing a flow of a predetermined quantity of fluid, flowing said entire predetermined quantity of said fluid through an upstream fluid flow portion to said dialyzer and from said dialyzer through a downstream fluid flow portion, producing a first constant flow in said upstream fluid flow portion, producing a second constant flow in said downstream portion, creating a pressure drop in said entire predetermined quantity of said fluid at a first predetermined location in said upstream fluid flow portion from a first predetermined substantially constant pressure to a second lower pressure, pumping said upstream fluid flow portion from a position downstream of said first predetermined location, measuring said second lower pressure, creating a pressure drop in said entire predetermined quantity of said fluid at a second predetermined location in said downstream fluid flow portion from a third pressure to a fourth predetermined substantially constant lower pressure, pumping said downstream fluid flow portion from a position upstream of said second predetermined location, measuring said third pressure, and controlling the flow of said fluid in said upstream and downstream fluid flow portions, based upon said measured second pressure and said measured third pressure, respectively.

28. The method of claim 27 including conducting ultrafiltration across said membrane in said dialyzer, said controlling of said flow of said fluid in said upstream and downstream fluid flow portions thereby controls the rate of said ultrafiltration in said dialyzer.

* * * * *